United States Patent
Allmendinger et al.

(10) Patent No.: US 8,712,006 B2
(45) Date of Patent: Apr. 29, 2014

(54) METHOD AND CT DEVICE FOR COMPUTER TOMOGRAPHIC SPIRAL SCANNING OF A PATIENT

(75) Inventors: Thomas Allmendinger, Forchheim (DE); Thomas Flohr, Uehfield (DE)

(73) Assignee: Siemens Aktiengesellschaft, Munich (DE)

( * ) Notice: Subject to any disclaimer, the term of this patent is extended or adjusted under 35 U.S.C. 154(b) by 381 days.

(21) Appl. No.: 13/249,483

(22) Filed: Sep. 30, 2011

(65) Prior Publication Data

US 2012/0082291 A1 Apr. 5, 2012

(30) Foreign Application Priority Data

Sep. 30, 2010 (DE) .......................... 10 2010 041 781

(51) Int. Cl.
*A61B 6/03* (2006.01)
(52) U.S. Cl.
CPC ....................................... *A61B 6/03* (2013.01)
USPC ...................... 378/15; 378/8; 378/9; 382/131
(58) Field of Classification Search
CPC ....................................................... A61B 6/03
USPC ................................ 378/4, 8–9, 15; 382/131
See application file for complete search history.

(56) References Cited

U.S. PATENT DOCUMENTS

| 2009/0141855 A1 | 6/2009 | Bruder et al. |
| 2010/0054395 A1 | 3/2010 | Noshi et al. |

FOREIGN PATENT DOCUMENTS

DE 102007056801 A1 6/2009

OTHER PUBLICATIONS

Flohr et al., Dual-source spiral CT with pitch up to 3.2 and 75 ms temporal resolution: Image reconstruction and assessment of image quality, Published Nov. 23, 2009, Medical Physics, vol. 36, No. 12, pp. 5641-5653.*
Christner et al., Dose Reduction in Helical CT: Dynamically Adjusted z-Axis X-ray Beam Collimation, Jan. 2010, AJR, vol. 194, pp. W49-W55.*
PTO 14/0077, Translation of German Office action.*
German Priority Document DE 10 2010 041 781.5, published Sep. 30, 2010.

* cited by examiner

*Primary Examiner* — Toan Ton
*Assistant Examiner* — John Corbett
(74) *Attorney, Agent, or Firm* — Harness, Dickey & Pierce

(57) ABSTRACT

An embodiment of the invention relates to a method and to a CT device for computer tomographic spiral scanning of a patient in the region of a moving organ, in particular a beating heart, wherein a pitch is adjusted which is less than the maximum pitch, with which 180° image data can still be reconstructed. In at least one embodiment, during the scan the evaluated detector data with respect to its z width and position on the at least one irradiated detector are restricted as a function of the projection angle in such a way that an effective virtual detector with smaller z width and with a z speed profile, which differs from the z speed profile of the real detector, is produced respectively, and the moving organ is reconstructed on the basis of the detector data of the at least one virtual detector.

19 Claims, 4 Drawing Sheets

METHOD AND CT DEVICE FOR COMPUTER TOMOGRAPHIC SPIRAL SCANNING OF A PATIENT

PRIORITY STATEMENT

The present application hereby claims priority under 35 U.S.C. §119 on German patent application number DE 10 2010 041 781.5 filed Sep. 30, 2010, the entire contents of which are hereby incorporated herein by reference.

FIELD

At least one embodiment of the invention generally relates to a method and to a CT device for computer tomographic spiral scanning of a patient in the region of a moving organ, in particular a beating heart, including a CT device with at least one detector.

BACKGROUND

CT devices and methods for spiral scanning of a patient, in particular also for movement-triggered spiral scanning and tomographic depiction of a beating heart, are generally known. Reference is made by way of example in this regard to document DE 10 2007 056 801 A1.

A fundamental problem with these known devices and methods resides in the still insufficient time resolution for imaging a heart with normal heart rate in the region of about 80 beats per minute and more in a resting phase. Attempts are therefore being made to equip CT devices with ever wider detectors, wherein, according to the currently used procedures, the feed rate or the pitch also increases ever more strongly during a scan, and, owing to the high acceleration forces associated therewith which act on the patient before the scan or as it begins, are reaching their limits and lead to adverse side effects.

SUMMARY

In at least one embodiment of the invention, a scanning method is disclosed with which, even in the case of relatively high heart rates, a shorter total recording time compared with previous flash spirals and a depiction of the heart that is low in movement artifacts may be achieved with future dual source CT devices with wider detectors, without the feed rate having to be increased compared with the previous prior art.

Advantageous developments of the invention are the subject matter of the subordinate claims.

The inventors recognized the following:

It has been found that instead of the maximum pitch of about 1.5 in the case of a single source CT device, a maximum pitch of 3.2-3.4 can be attained with a dual source CT device as a function of the reconstructed measuring field. The pitch is the feed per revolution divided by the collimated width of the detector in the z direction. In the case of a detector with 64×0.6 mm collimation as an example, the collimated width in the z direction, also called the z width, is 38.4 mm. With a maximum pitch, data from about a quarter rotation per detector are used for image reconstruction in the case of a dual source CT device. The time resolution of the images generated with this scan mode is therefore about a quarter of the rotation time of the dual source CT device. It is possible to start the data recording at a z position that can be chosen by the user, for example the base of the heart, in a phase of the patient's cardiac cycle chosen by the user. With a sufficiently large z width of the two detectors, for example 64×0.6 mm per detector, it is therefore possible to record the whole of the patient's heart in a predefined cardiac phase in just one cardiac cycle.

In the case of two detectors with 64×0.6 mm collimation and 0.285 s rotation time respectively, the maximum table feed at pitch 3.2-3.4 for example is about 430-460 mm/s. The heart with a z extension of about 12 cm can thus be covered in about 0.26-0.28 s. To this is added the recording time of an image of, in this example, about 75 ms, and this corresponds to a total data recording time of about 0.34-0.36 s. This time is sufficient to image the heart in the case of low heart rates in the resting phase (diastole) so as to be free from movement artifacts. This method is used as what is known as "flash spirals" in the SOMATOM Definition Flash belonging to the Applicant. However, the heart rate for this method has to be very low in the case of two detectors each with 64×0.6 mm collimation as in the "Definition Flash", typically following previous clinical experiences below 60 beats per minute. With higher heart rates the total data recording time is too long and parts of the heart volume are recorded in relatively more moving cardiac phases, and this leads to movement artifacts and therewith to results that can only be used to a limited extent clinically.

For broader use and greater stability of the flash spirals in the clinical routine, even with patients with higher heart rates, it is therefore very desirable to reduce the total recording time further, so that even in the case of higher heart rates the situation is avoided where parts of the heart volume are examined in moving cardiac cycles. This is basically possible by increasing the table feed of the flash spirals, and this may be achieved by widening the two detectors in the z direction. Two detectors with, for example, 128×0.6 mm collimation instead of 64×0.6 mm collimation would theoretically allow the feed rate to be doubled.

However, a further significant increase in the table feed above the currently maximum attained value of about 450 mm/s can only be achieved with great difficulty from a technical point of view because acceleration to the end speed must take place quickly on the one hand but on the other hand the acceleration movement must be acceptable to the patient. The prediction of the patient's ECG, which is necessary for ECG triggering, becomes more difficult as the acceleration time increases until the end speed is attained. If possible the prediction must be extended beyond two beats and becomes significantly more unreliable as a result. With a scan mode of this kind the total recording time would be reduced, but the correct positioning of the scan within the resting phase of the cardiac cycle would be much more difficult and the overall result would therefore potentially not be improved.

However, it is possible to disclose an alternative method with which the total recording time of what is known as a flash spiral for covering a scan area with length L may be reduced compared with the prior art in the case of a dual source CT device having two detectors widened in the z direction, for example 96×0.6 mm or 128×0.6 mm z coverage, without having to increase the table feed rate and without impairing the time resolution of the individual images.

This can take place as follows: a dual source CT device has two detectors each with $N_q$ detector rows of collimated width S. Parallel data with parallel projection angles θ result by azimuthal rebinning of the data recorded in fan geometry with a fan projection angle α. A projected detector in the turning center is considered in parallel geometry below. The maximum possible pitch $p_{max}$ is determined by the requirement that the beam at the edge of the measuring field of the uppermost detector row of detector B with the parallel coordinate $b_{max} = -R_F \beta_{max}$ and the complementary beam at the edge of the measuring field of the lowest detector row of detector A are spaced apart from each other by less than a collimated layer thickness S. Here $\beta_{max}$ denotes the maximum fan angle in the desired measuring field, $R_F$ the spacing of the tube focus from the turning center of the CT scanner and q=0 the row number. The complementary beam at the edge of the measuring field of the lowest detector row of detector A is defined by the parallel coordinate $\tilde{b}_{max}=R_F\beta_{max}$ and the row number $q=N_q-1$, following a quarter rotation of the measuring system in the z direction to allow a well-defined spiral interpolation. Such a situation is shown in FIG. 1. The arrow points toward the previously described intersection of the projected detectors at maximum pitch.

A maximum pitch of $$p_{max}^{DSCT} = \frac{2\pi(1 + (N_q - 1)\cos\beta_{max})}{N_q(2\beta_{max} + \frac{\pi}{2})}$$

is obtained as a function of the maximum fan angle $\beta_{max}$, i.e. the desired diameter of the measuring field.

In the turning center, for $\beta_{max}=0$, the maximum pitch is 4. For $\beta_{max}\sim 9°$, this corresponds to a cardio measuring field of about 180 mm diameter, a pitch of about 3.4 can be chosen.

In the case of two detectors each with 64×0.6 mm collimation and 0.285 s rotation time, a feed rate of 458 mm/s results therefore.

In the case of the cardio CT the spiral scan is triggered by the patient's ECG such that the data recording at a z position $z_0$, which can be chosen by the user, for example the base of the heart, starts in a phase of the patient's cardiac cycle which can be chosen by the user. A starting angle $\alpha_0$ of the projection angle interval of detector A, which is used for reconstruction of the image at the z position $z_0$, forms part of this z position $z_0$. The starting angle of the projection angle interval of detector B is offset by exactly 90°. Overall the projection angle interval used per detector for an image has the minimum length $\pi/2+2\beta_{max}$, for $\beta_{max}\sim 9°$ this is therefore about 108°.

Owing to the maximum pitch chosen for this $\beta_{max}$ the starting angle for the next image, which is reconstructed at the z position $z_0+\Delta z$, is shifted with respect to $\alpha_0$ by $\Delta\alpha$. This corresponds to a phase shift in the cardiac cycle of the patient. Successive images are therefore slightly staggered in terms of time. The time shift from the first image at position $z_0$ to the last image at position $z_0+L-L$ corresponds to the length of the scan area—plus the time for recording an image therefore determines the total recording time of the scan. This situation is shown in FIG. 2.

The angular shift $\Delta\alpha$ is calculated as follows:

$$\Delta\alpha = 2\pi \frac{\Delta z}{p_{max}N_q S}.$$

For $\Delta z=120$ mm corresponding to a required scan area for the heart of L=120 mm, $\Delta\alpha=331°$ results with $p_{max}=3.4$, $N_q=64$ and S=0.6 mm. If the minimum projection angle interval per image $\pi/2+2\beta_{max}$, i.e. about 108° for $\beta_{max}\sim 9°$, is added, the overall angular range of the scan of 439° is obtained. With a rotation time of 0.285 s this corresponds to a total recording time of 348 ms.

If the detector were simply to be widened, i.e. for example $N_q=128$ and S=0.6 mm chosen, a maximum feed rate of 916 mm/s would result at a pitch $p_{max}=3.4$, and according to the above calculation a total angular range of the scan of 166°+108°=274°, corresponding to a shortened total recording time of 217 ms with a rotation time of 0.285 s. This situation is shown in FIG. 3. Such a high feed rate cannot be achieved technically, however, if, simultaneously, a short acceleration phase of one second duration at most, and at the same time a gentle acceleration that is tolerated by the patient are demanded.

This dilemma may be resolved if—as is possible with an over-wide pair of detectors—during the scan by the real detector at a first speed, the detector surfaces or detector signals are used as if a virtual, narrower detector at a speed higher than the actual detector scans the patient. This higher, mean speed, or a speed profile generating this mean speed, is preferably selected such that at the start of the scan the last detector row in the scanning direction matches the last detector row of the virtual detector and at the end of the scan the leading detector row of the real detector matches the leading detector row of the virtual detector.

A dual source CT device has two detectors each with $N_q$ detector rows with collimated width S, based on the above described example $N_q=128$ and S=0.6 mm. The CT device is operated with a flash spiral having a pitch p less than the maximum pitch $p_{max}$, which is reliable for the chosen fan angle $\beta_{max}$. By way of example, the CT device can be operated with pitch p=1.7, so the feed rate in the illustrated example is still 458 mm/s with a rotation time of 0.285 s and is therefore just as high as the maximum feed rate for a dual source CT device with just 64 rows.

Due to the smaller pitch, a projection angle interval for reconstruction of an image is available at each z position which is greater than the minimum projection angle interval $\pi/2+2\beta_{max}$. The available projection angle interval is approximately $\Delta\alpha=2\pi/p$, for p=1.7 the maximum projection angle interval per image is therefore about 212°.

If this maximum projection angle interval is not completely used and instead only the minimum projection angle interval $\pi/2+2\beta_{max}$ continues to be used for reconstruction of an image, an improved time resolution may be attained. By skillful selection and image position-dependent shifting of these minimum projection angle intervals within the maximum permissible projection angle interval, the starting angle for successive images, which are offset in the z position by $\Delta z$, can also be shifted by less than $\Delta\alpha$ to therefore minimize the total recording time for the scan.

For reconstruction of an image at the z position $z_0$, by way of example, the starting angle $\alpha_0$ which corresponds to the start of the maximum projection angle interval is not used and instead a starting angle $\alpha_0'=\alpha_0+2\pi/p-\pi/2-2\beta_{max}$ shifted within this maximum projection angle interval is used.

A smaller angular shift $\Delta\alpha'$ is accordingly chosen for the next image at z position $z_0+\Delta z$, which is calculated as follows $$\Delta\alpha' = 2\pi\frac{\Delta z}{pN_q S} - \frac{2\pi}{p} + \frac{\pi}{2} + 2\beta_{max}.$$

This situation is shown in FIG. 4.

For $\Delta z=120$ mm (total scan area of the heart where L=120 mm), p=1.7, $N_q=128$ and S=0.6 mm, $\Delta\alpha=227°$. If the minimum projection angle interval per image $\pi/2+2\beta_{max}$, for $\beta_{max}\sim 9°$ about 108° therefore, is added the total angular range of the scan is 335°. With a rotation time of 0.285 s this leads to a total recording time of only 265 ms, although the feed is not higher than with a detector with $N_q=64$ and $p_{max}=3.4$ and a corresponding total recording time of 348 ms.

To increase the dose efficiency of such a scanning mode it is expedient to fade in precisely the region used by way of two beam-side diaphragm jaws that can be moved in the z direction and can be controlled independently of each other on the detector for each projection angle α, and to fade out regions which are not used. This is schematically shown in FIG. 5. The regions faded out by the two beam-side diaphragm jaws on the detector are shown there for four different projection angles as thick black bars.

According to this above-described basic idea, the inventors are proposing a method, in at least one embodiment, for computer tomographic spiral scanning of a patient in the region of a moving organ, in particular a beating heart, having a CT device with at least one detector, comprising the following method steps:

carrying out a spiral scan at a pitch which is less than the maximum pitch, with which 180° image data can still be reconstructed, using at least one detector having a predefined z width and a beam directed thereon, wherein during the scan the evaluated detector data z width and position on the at least one irradiated detector are restricted as a function of the projection angle in such a way that an effective virtual detector with smaller z width and with a z speed profile, which differs from the z speed profile of the real detector, is produced respectively, and the region of the moving organ is reconstructed on the basis of the detector data of the at least one virtual detector.

Reference is made to the fact that the definition of the maximum pitch, at which 180° image data can still be reconstructed, is firstly dependent on the type of CT system with respect to the number of ray-detector systems and secondly, even with this examination, possibilities for inter-polation of data, which are produced by scanning gaps, are to be ignored. It should therefore correspond to the maximum pitch of a feed rate at which a reconstruction of 180° image data is still possible but no unnecessary scanning redundancies are produced. Starting from this definition the terms "maximum pitch" and "maximum feed rate" described here are clear to a person skilled in the art.

As a result of this measure the virtual detector actually used for data generation of the tomographic data to be reconstructed can be operated at a high and optionally variable "virtual" speed, while the very wide, real detector that is actually to be mechanically moved must be accelerated and moved at comparatively low speeds in the system axis direction. On the one hand this avoids the necessity for an extremely stable mechanical construction as well as sparing the patient from high acceleration effects which could also lead to undesirable movement artifacts.

It is advantageous to perform a scan with the lowest possible dose rate and not to apply an unused dose if the detector data is restricted by limiting the beam with respect to its z width and position as a function of projection angle by way of variable and controlled diaphragms.

A mean pitch can also be used for the at least one virtual detector which is greater than the mean pitch of the associated real detector, the mean pitch being measured between the start and end of the scan respectively.

The z speed profile of at least one virtual detector can also be adapted to the z speed profile in such a way that at the start of the scan the last detector row, viewed in the z direction, of the real detector matches the last detector row of the virtual detector and at the end of the scan the leading detector row of the real detector matches the leading detector row of the virtual detector. This makes optimum use of the detector surface of the real detector.

Furthermore, the scan and the movement of the virtual detector carried out in the process can be performed such that at least one real detector is accelerated before the scan to a constant pitch during the scan. Alternatively the at least one real detector can be constantly accelerated up to the end of the scan or up to the middle of the scan and is constantly decelerated from the middle of the scan onwards.

If, by way of example, a start region and an end region of the heart are to be scanned particularly well, while a region which is of less interest is located therebetween, the speed profile of the at least one virtual detector can be chosen such that at the start and end of the scan it is advanced more slowly in the z direction over predefined sections and is advanced more quickly between the sections. Of course this method is not restricted to just the start and end regions. Basically a region that is to be more intensively examined can be scanned by the virtual detector at a relatively low feed rate, while less interesting regions can be passed through quickly or may even be skipped without reconstruction respectively. Accordingly the inventive speed profile of the virtual detector is completely variable and largely independent of the speed profile or constant movement of the real detector.

Embodiments of the inventive method described here is basically applicable to one or multi-detector systems. It is advantageous if at least two real detectors with at least two associated beams are used.

Furthermore, the scan can be triggered in a manner known per by a physiological signal, by way of example an ECG signal or a respiratory signal of the patient may be used.

It is also proposed that the scan takes place with at least two different mean radiant energies and/or at least the reconstruction is carried out with respect to at least two different mean radiant energies. An energy-selective detector in particular may also be used for this purpose.

In addition to embodiments of the inventive method, in at least one embodiment the inventors are also proposing a CT device for computer tomographic spiral scanning of a patient in the region of a moving organ, in particular a beating heart, comprising the following features:

at least one detector arranged on a gantry and rotating around a z axis, having a beam directed thereon, wherein diaphragms are provided which during the scan restrict the beam as a function of the projection angle with respect to its z width and position on the at least one irradiated detector, and a controller which is programmed such that an active virtual detector with smaller z width and with a z speed profile, which differs from the z speed profile of the real detector, is produced.

With at least one embodiment of this inventive CT device, a reconstruction device may also be present which reconstructs at least one region of the moving organ on the basis of the detector data of the at least one virtual detector.

Finally, in at least one embodiment, the CT device can comprise two or three real angularly offset detectors on the gantry, and devices for forming two or three virtual detectors.

BRIEF DESCRIPTION OF THE DRAWINGS

The invention will be described in more detail hereinafter with reference to the example embodiments and with the aid of the figures, with only the features required for understanding the inventive being shown. The following reference characters are used: 1: dual source CT device; 2: first X-ray tube; 3: first detector; 4: second X-ray tube; 5: second detector; &: gantry housing; 7: patient; 8: patient couch; 9: system axis; 10: computer; 11: contrast medium applicator; 12: ECG lead;

A,B: projecting detectors; B1, B2: diaphragms; I: projection angle intervals; Db: detector width; $Prg_1$ to $Prg_n$: computer programs; Sb: scan area; Vo: detector top; Vu: detector bottom; α: projection angle; β: fan angle.

In detail in the drawings:

Figure 1:
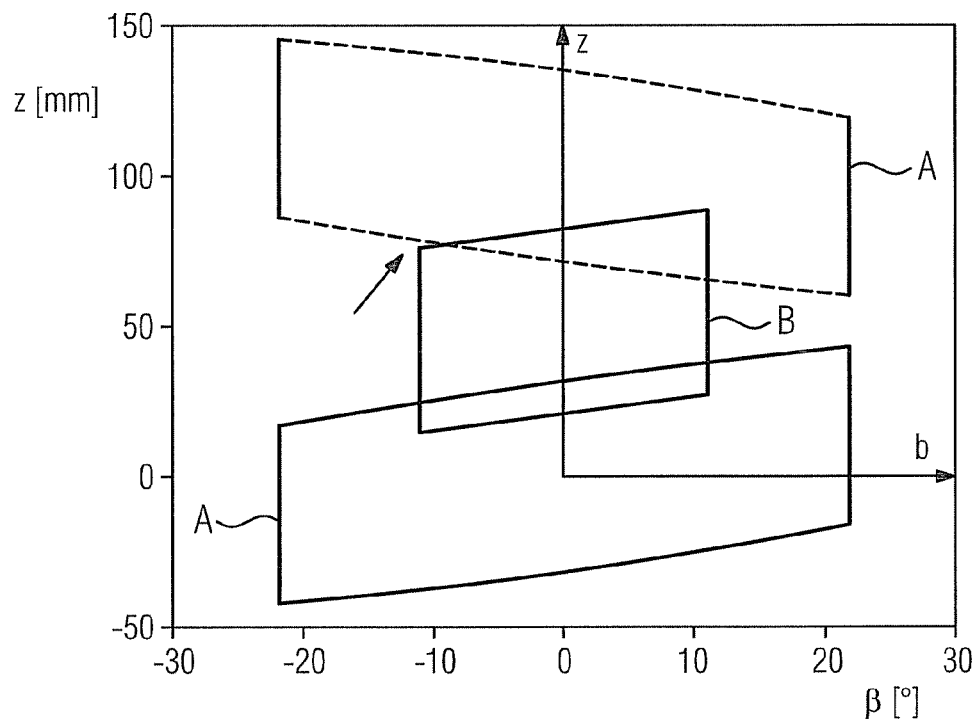
Figure 2:
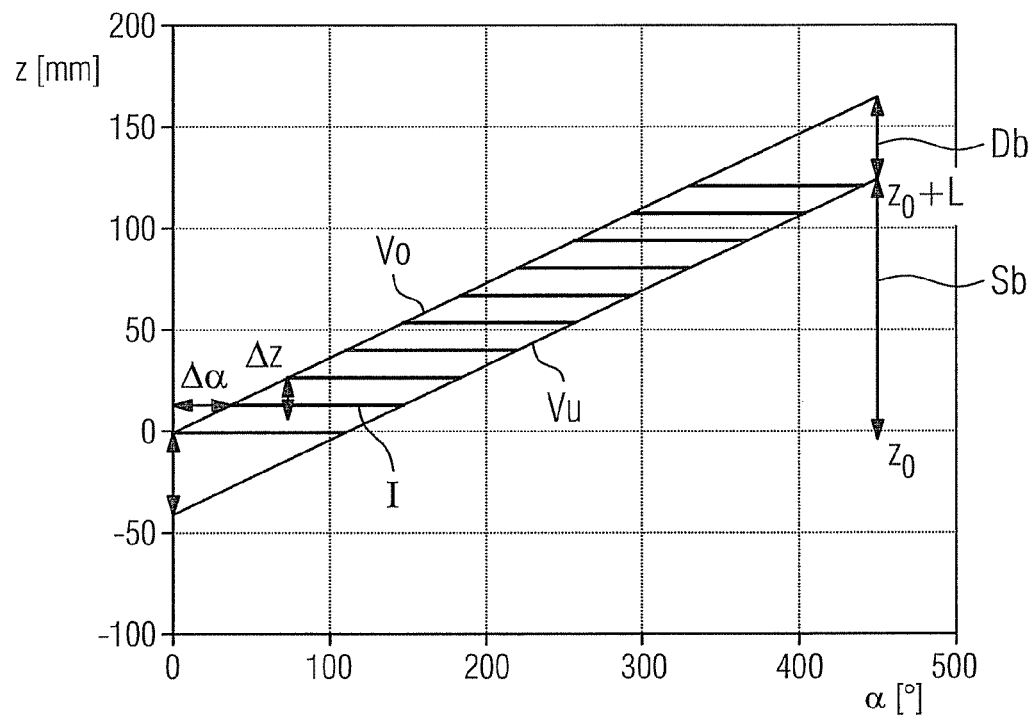
Figure 3:
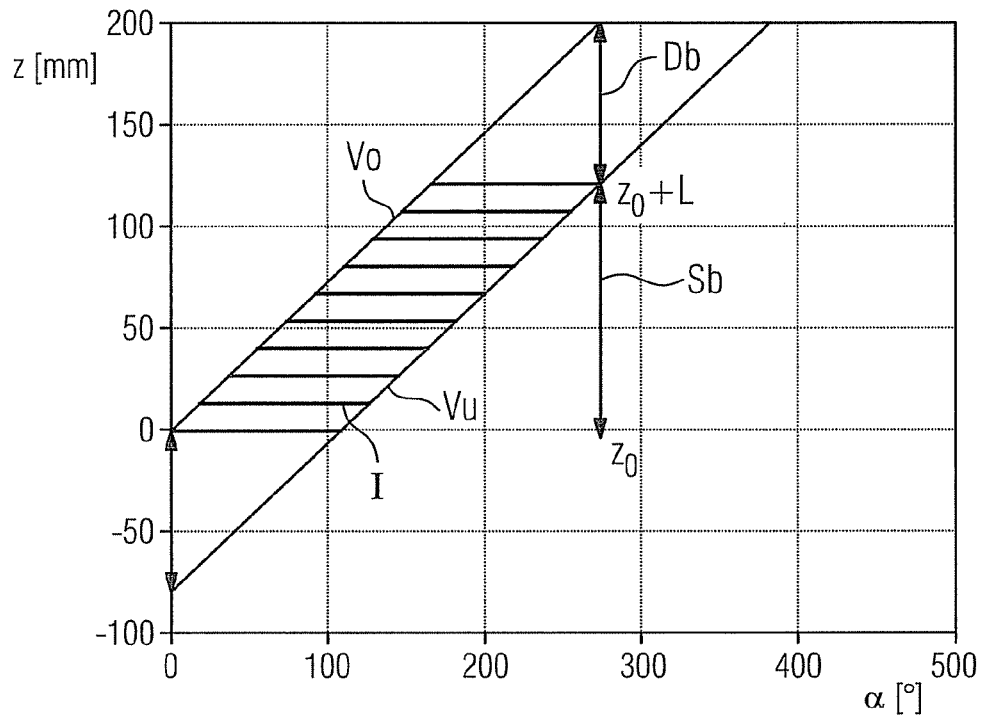
Figure 4:
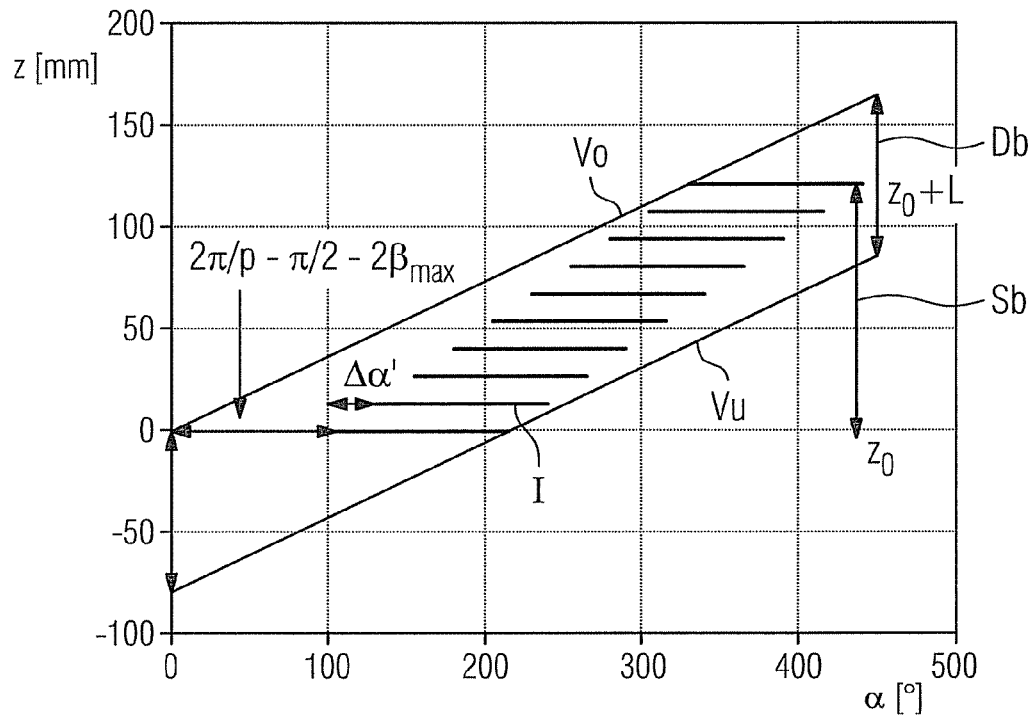
Figure 5:
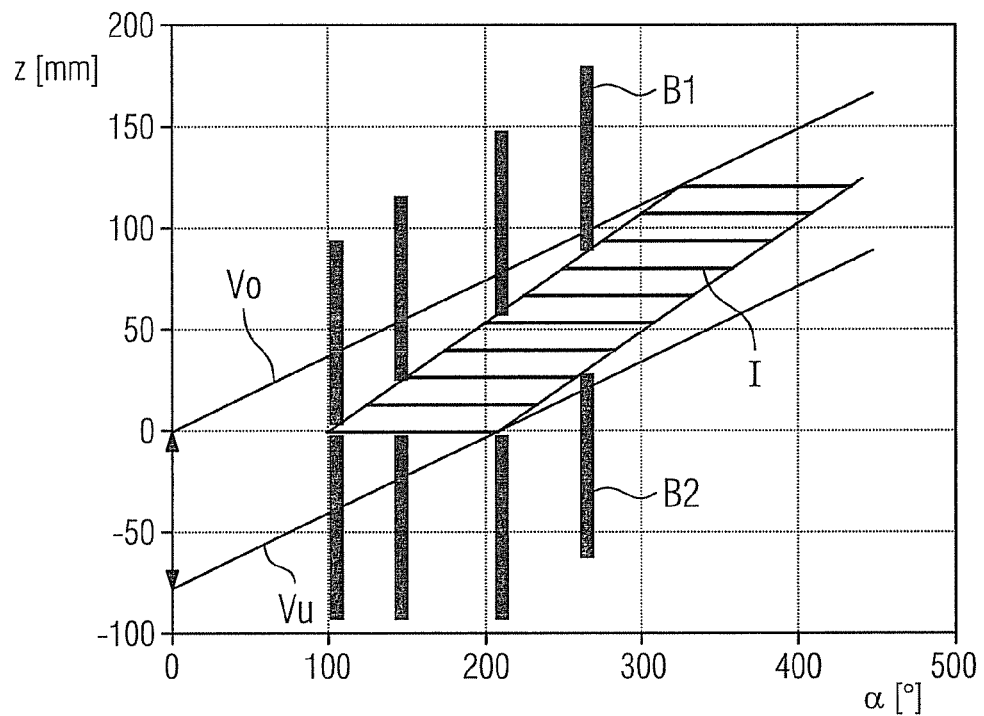
Figure 6:
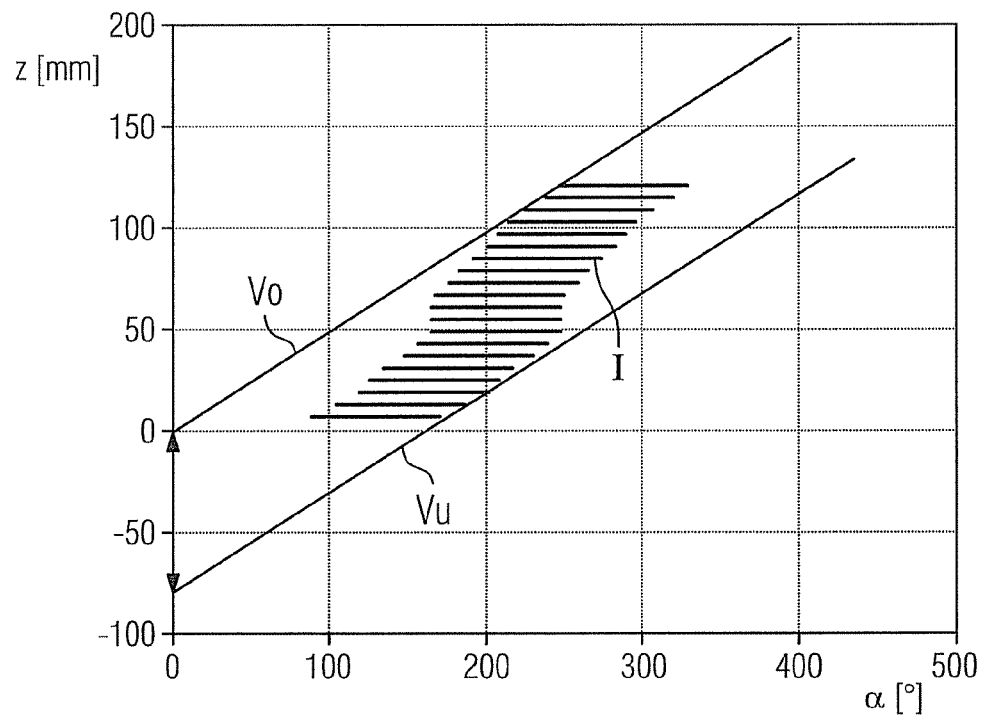
Figure 7:
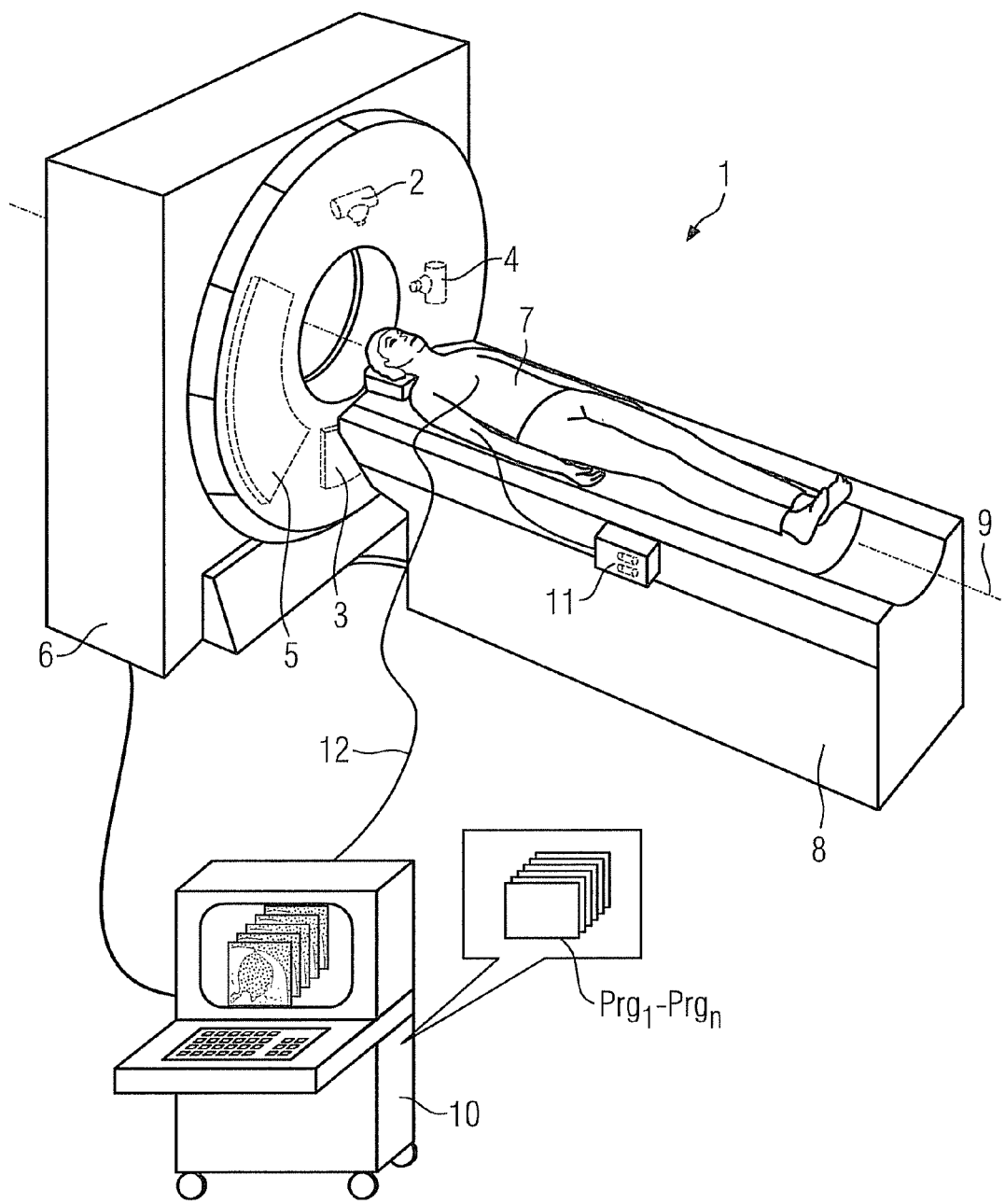

FIG. 1: shows a graph of two projected detectors—not restricted according to an embodiment of the invention—in the turning center of a dual source CT device;

FIG. 2: shows a graph of the spiral scanning of a detector of z width 64×0.6 mm=38.4 mm of a dual source CT device with a feed corresponding to the maximum pitch 3.4 for $\beta_{max}=9°$;

FIG. 3: shows a graph of a detector of z width 128×0.6 mm=76.8 mm of a dual source CT device with the maximum pitch $p_{max}=3.4$ for $\beta_{max}=9°$ with continuous feed;

FIG. 4: shows an embodiment of an inventive variant of a scanning with the regions of the real detector used by the virtual detector;

FIG. 5: shows by way of solid bars top and bottom, an embodiment of an inventive variant of a scanning in which the regions of the real detector not used by the virtual detector limit with the aid of two diaphragm jaws B1 and B2 the area scanned by the virtual detector;

FIG. 6: a further variant of the characteristic of the projection angle intervals I of the virtual detector used for reconstruction of the image data;

FIG. 7: shows an embodiment of an inventive dual source CT device with two focus-detector systems.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

POW Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows two projected detectors—not restricted according to embodiments of the invention—in the turning center of a dual source CT device. The fan angle β is shown on the abscissa against the z coordinate of the CT device on the ordinate. The maximum pitch results here from the condition that beams at the edge of the measuring field of detector B and complementary beams from detector A are spaced apart from each other by less than a layer thickness S, i.e. there is an overlapping point, as is shown by the arrow.

FIG. 2 shows the spiral scanning of a detector of z width 64×0.6 mm=38.4 mm of a dual source CT device with a feed, corresponding to the maximum pitch 3.4 for $\beta_{max}=9°$. The characteristic of the z positions of the detector bottom Vu corresponding to the last detector row and the detector top Vo corresponding to the first detector row are shown as a function of the projection angle. The scan area Sb extends from $z_0$ to $z_0+L$. The detector width in the z direction is designated Db. In the illustrated case L=120 mm, corresponding to the z extension of a heart. Inside the characteristics Vo and Vu are shown the projection angle intervals I of the detector which are each used for reconstruction of a sectional view. The projection angle intervals of images offset by Δz in the z direction are shifted by Δα. The overall recording of the scan data extends in this case over an angle of 331°+108°=439°, which corresponds with the rotation time 0.285 s to the total recording time of 348 ms.

FIG. 3 shows a continuous feed of a detector of z width 128×0.6 mm=76.8 mm of a dual source CT device with maximum pitch $p_{max}$=3.4 for $β_{max}$=9°. Again the characteristic of the z position of the detector bottom and top Vu and Vo are shown on the abscissa as a function of the projection angle α. The scan area extends from $z_0$ to $z_0$+L. In the illustrated case the scan area Sb has a length of L=120 mm, corresponding to the z extension of the heart. The respective projection angle intervals, which are used per detector for an image, are shown as lines and identified by the reference character I. The overall recording of the scan data extends in this case over an angle of 166°+108°=274°, which corresponds with the rotation time 0.285 s to the total recording time of 217 ms.

FIG. 4 shows the feed of a detector of z width 128×0.6 mm=76.8 mm of a dual source CT with a pitch p, which is smaller than the maximum pitch $p_{max}$=3.4 for $β_{max}$=9°. In this case p=1.7. The z position of the detector bottom and top Vu and Vo is again shown on the ordinate as a function of the projection angle α on the abscissa. The scan area extends from $z_0$ to $z_0$+L where L=120 mm, corresponding to the z extension of the heart. Although there is a larger projection angle interval at each z position, only the minimum projection angle interval $π/2+2β_{max}$ detector is used for image reconstruction. These projection angle intervals are shown as lines and denoted by reference character I. The starting angle $α_0$ which corresponds to the start of the maximum projection angle interval, is not used for reconstruction of an image at the z position $z_0$ and instead a shifted starting angle of $α_0'=α_0+2π/p-π/2-2β_{max}$ is used. A smaller angular shift Δα' is accordingly chosen for the next image at the z position $z_0$+Δz. The overall recording of the scan data extends in this case over an angle of 227°+108°=335°, which corresponds with the rotation time 0.285 s to the overall recording time of 265 ms.

This graph therefore shows how a relatively narrow virtual detector—or in other words, a narrower detector range—, which has a significantly faster virtual feed rate than the real detector, can be "fitted" in a real, very wide detector with a first relatively slow feed rate. Since the virtual detector does not have any mechanical parts which have to be moved at the feed rate of the virtual detector, no acceleration forces that are unacceptable to a patient are produced either.

While the detector regions not used for the virtual detector, and therewith the unused region of the beam used with which the patient is X-rayed, is not given further consideration in FIG. 4, FIG. 5 shows an embodiment of an inventive variant of scanning with real radiation shading of detector regions that are not required. To avoid unnecessary dose rates the regions of the real detector not used by the virtual detector are limited here with the aid of two diaphragm jaws B1 and B2—shown by solid bars—the area scanned by the virtual detector. There is therefore a fading-out on the real detector of the regions not used for image reconstruction by way of two moving radiator-side diaphragm jaws B1 and B2 which can be controlled independently of each other. The two radiator-side diaphragm jaws B1 and B2 are shown for four different projection angles α. As may be seen from the graph, the two diaphragm jaws have to be controlled in such a way that they open and close again asynchronously. The mechanical stress on the CT system due to this diaphragm movement can largely be ignored in this connection.

FIG. 6 finally shows in the same manner of depiction as in FIGS. 4 and 5 the characteristic of the projection angle intervals I of the virtual detector used for reconstruction of the image data, wherein by appropriate selection of the detector data, optionally with an correspondingly executed fading-out of the beam by control of the diaphragm jaws, a variable feed rate of the virtual detector is attained which—varies during the scans.

In the example shown here a z position-dependent optimization of the position of the projection angle intervals I used for image reconstruction is carried out within the cardiac cycle of the patient while maintaining a minimum total recording time for data recording. The virtual detector is moved at the start and end of the scan at a feed rate which matches the feed rate of the real detector. Optimal image representation is achieved in this region. The virtual detector is greatly accelerated in an intermediate region, however, and is moved at a higher feed rate, although this results in reduced image quality but this is a region of the heart which seems to be less relevant to the observer.

Finally, FIG. 7 shows an example of an embodiment of an inventive dual source CT device 1 with two focus-detector systems, which is equipped for carrying out the inventive method. The two focus-detector systems equipped with wide detectors are formed by a first X-ray tube 2 with an opposing detector 3 and by a second X-ray tube 4 with a further opposing detector 5. The focus-detector systems are arranged on the gantry so as to be angularly offset by 90° and are located in the gantry housing 6. The patient 7 is located on patient couch 8 and in the course of the inventive examination during the scan is pushed along the system axis 9 and through the centrally arranged measuring field, so a spiral scan takes place relative to the patient. According to an embodiment of the invention the focus-detector systems can also comprise diaphragm jaws (not shown here) which inventively restrict the beam issuing from the X-ray tube.

For ECG-triggered scanning an ECG evaluation may also be provided in the computer 10 which with the aid of the ECG scan line 12 attached to the patient can evaluate the ECG signals of the patient 7 and control the CT device accordingly. A contrast medium applicator 11 is also located on the patient couch 8 and controlled by the computer can, if required, make a corresponding contrast medium application.

The entire system is controlled by computer programs $Prg_1$-$Prg_n$, which are stored in a memory which the computer 10 can access. Program codes are also located in this memory which can execute embodiments of the inventive scan and evaluation of the detector data, including their reconstruction, during operation of the system.

Overall, a method and a CT device for computer tomographic spiral scanning of a patient in the region of a moving organ, in particular a beating heart, is therefore described by embodiments of the invention, wherein a pitch is adjusted, which is smaller than the maximum pitch, with which 180° image data can still be reconstructed, and during the scan the utilized detector data can be restricted with respect to its z width and position on the at least one irradiated detector as a function of projection angle in such a way that a respective effective virtual detector with smaller width and with a z speed profile, which differs from the z speed profile of the real detector, is produced and the moving organ is reconstructed on the basis of the detector data of the at least one virtual detector.

By way of addition, reference is made to the fact that, owing to the desired high time resolution, the scans and image reconstructions described here primarily relate to complete scans over an angular range of 180° plus fan angle (=180° scan) and accordingly detector data from a projection interval of a total of 180° per image (=180° image) is used with the reconstructions.

It is understood that the features of embodiments of the invention cited above can be used not only in the respective combinations disclosed but also in other combinations or alone, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for computer tomographic spiral scanning of a patient in the region of a moving organ, using a CT device with at least one detector, comprising:
   carrying out a spiral scan at a pitch, which is less than a maximum pitch, with which 180° image data is still reconstructable, using at least one detector including a predefined z width and a beam directed thereon, wherein during the scan, evaluated detector data with respect to the z width and position on the at least one irradiated detector are restricted as a function of the projection angle in such a way that an effective virtual detector with a relatively smaller z width and with a z speed profile, which differs from a z speed profile of the at least one detector, is produced respectively; and
   reconstructing the region of the moving organ on the basis of the detector data of the at least one virtual detector.

2. The method as claimed in claim 1, wherein the detector data is restricted in that, with respect to its z width and position, the beam is limited as a function of the projection angle by variable and controlled diaphragms.

3. The method as claimed in claim 1, wherein a mean pitch is used for the at least one virtual detector which is relatively greater than the mean pitch of the associated real detector, the mean pitch being measured between the start and end of the scan respectively.

4. The method as claimed in claim 1, wherein the z speed profile of at least one virtual detector is adapted to the z speed profile in such a way that at the start of the scan the last detector row, viewed in the z direction, of the at least one detector matches the last detector row of the virtual detector and at the end of the scan the leading detector row of the at least one detector matches the leading detector row of the virtual detector.

5. The method as claimed in claim 1, wherein the at least one detector is accelerated before the scan to a constant pitch during the scan.

6. The method as claimed in claim 1, wherein the at least one detector is constantly accelerated up to the end of the scan.

7. The method as claimed in claim 1, wherein the at least one detector is constantly accelerated up to the middle of the scan and is constantly decelerated from the middle of the scan onwards.

8. The method as claimed in claim 1, wherein the at least one virtual detector is advanced more slowly in the z direction over predefined sections at the start and end of the scan and is advanced relatively more quickly between the sections.

9. The method as claimed in claim 1, wherein the at least one detector includes at least two detectors including at least two respective associated beams are used.

10. The method as claimed in claim 1, wherein the scan is triggered by a physiological signal.

11. The method as claimed in claim 10, wherein an ECG signal of the patient is used as the physiological signal.

12. The method as claimed in claim 10, wherein a respiratory signal of the patient is used as the physiological signal.

13. The method as claimed in claim 1, wherein the scan takes place with at least two different mean radiant energies.

14. The method as claimed in claim 1, wherein the reconstruction takes place with respect to at least two different mean radiant energies.

15. A non-transitory computer readable medium including program segments for, when executed on a computer device, causing the computer device to implement the method of claim 1.

16. A CT device for computer tomographic spiral scanning of a patient in the region of a moving organ, comprising:
- at least one detector arranged on a gantry and rotating around a z axis, having a beam directed thereon, wherein diaphragms are provided which, during the scan, restrict the beam with respect to its z width and position on the at least one irradiated detector as a function of the projection angle; and
- a controller, programmed such that an active virtual detector, with a relatively smaller z width and with a z speed profile which differs from a z speed profile of the at least one detector, is produced.

17. The CT device as claimed in claim 16, wherein a reconstruction device is provided which reconstructs at least one region of the moving organ on the basis of detector data of the at least one virtual detector.

18. The CT device as claimed in claim 16, wherein the at least one detector includes two or three real angularly offset detectors, arranged on the gantry and devices for forming two or three virtual detectors are attached.

19. The CT device as claimed in claim 16, wherein the at least one detector includes two or three real angularly offset detectors, arranged on the gantry and devices for forming two or three virtual detectors are attached.

* * * * *

UNITED STATES PATENT AND TRADEMARK OFFICE
CERTIFICATE OF CORRECTION

PATENT NO. : 8,712,006 B2  Page 1 of 1
APPLICATION NO. : 13/249483
DATED : April 29, 2014
INVENTOR(S) : Thomas Allmendinger It is certified that error appears in the above-identified patent and that said Letters Patent is hereby corrected as shown below:

Title Page, item (54) and in the Specification, Column 1, title should read as follows:
METHOD AND CT DEVICE FOR COMPUTER TOMOGRAPHIC SPIRAL SCANNING OF A PATIENT Signed and Sealed this
Sixteenth Day of September, 2014

Michelle K. Lee
*Deputy Director of the United States Patent and Trademark Office*